United States Patent [19]

Kligman

[11] Patent Number: 4,603,146

[45] Date of Patent: Jul. 29, 1986

[54] METHODS FOR RETARDING THE EFFECTS OF AGING OF THE SKIN

[76] Inventor: Albert M. Kligman, c/o Department of Dermatology, University of Pennsylvania, Philadelphia, Pa. 19104

[21] Appl. No.: 759,505

[22] Filed: Jul. 26, 1985

Related U.S. Application Data

[63] Continuation of Ser. No. 610,711, May 16, 1984, abandoned, which is a continuation-in-part of Ser. No. 297,388, Aug. 28, 1981, abandoned.

[51] Int. Cl.⁴ .............................................. A61K 31/20
[52] U.S. Cl. ..................................... 514/559; 514/725
[58] Field of Search ................................ 514/559, 725

[56] References Cited

U.S. PATENT DOCUMENTS 3,729,568  4/1973  Kligman .............................. 424/318
3,856,934  12/1974 Kligman .............................. 424/62
3,906,108  9/1975  Felty ..................................... 424/318

FOREIGN PATENT DOCUMENTS 906000  9/1962  United Kingdom .

OTHER PUBLICATIONS

Thomas et al, J. Am. Acad. Dermatol., vol. 4, No. 5, pp. 505–513 (5–1981).
Kligman, A. M. & Willis, I. "A New Formula for Depigmenting Human Skin", *Archives of Dermatology*, 111:40–48 (Jan. 1975).
Kligman A. M., Plewig, G. & Mills, O. H., "Topically Applied Tretinoin for Senile (Solar) Comedones", *Archives of Dermatology*, 104: 420–421 (Oct. 1971).
Robinson T. A. & Kilgman, A. M., "Treatment of Solar Keratoses of the Extremities with Retinoic Acid and 5-Fluorouracil", *British Journal of Dermatology*, 92:703–705 (1975).
Kligman, L. H. & Kligman A. M., "The Effect on Rhino Mouse Skin of Agents which Influence Keratinization and Exfoliation", *Journal of Investigative Dermatology*, 73:354–358 (1979).

*Primary Examiner*—Leonard Schenkman
*Attorney, Agent, or Firm*—Panitch Schwarze Jacobs & Nadel

[57] ABSTRACT

Various effects of aging of skin due to impairment of differentiation of epidermal epithelial cells and loss of collagen fibers, abnormal changes in elastic fibers and deterioration of small blood vessels in the dermis of the skin are retarded by applying topically to the epidermis in a maintenance therapy program effective amounts of vitamin A acid (tretinoin) such that epithelial growths are substantially reduced and prevented and the skin substantially regains and maintains its firmness, turgor and elasticity. Moreover, with persistent treatment dermal blood cells and vessels increase and the epidermis and dermis thicken, resulting in improved ability of the skin to sense, resist and recover from irritation or injury. Further, hyperpigmentation, lines and wrinkles due to aging are reduced and prevented. The treatment is particularly useful for human facial skin and preferably applied in amounts insufficient to cause excessive irritation.

2 Claims, No Drawings

METHODS FOR RETARDING THE EFFECTS OF AGING OF THE SKIN

This application is a continuation of Ser. No. 610,711, May 16, 1984, now abandoned, which is a continuation-in-part of my co-pending application Ser. No. 297,388, filed Aug. 28, 1981, entitled "Composition and Method for Improving the Quality of Human Skin and Skin Aging Retardant", now abandoned.

FIELD OF THE INVENTION

This invention relates to methods using vitamin A acid to retard the effects of aging of the skin and generally improve the quality of the skin, particularly human facial skin.

BACKGROUND OF THE INVENTION

Caucasians who have had a good deal of sun exposure in childhood will show the following gross cutaneous alterations in adult life: wrinkling, leatheriness, yellowing, looseness, roughness, dryness, mottling (hyperpigmentation) and various premalignant growths (often subclinical). These changes are most prominent in light-skinned persons who burn easily and tan poorly. The baleful effects of sunlight are cumulative, increasing with time. Although the anatomic degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness, loss of elasticity are very late changes.

It is known to use vitamin A acid for the treatment of acne as set forth in my U.S. Pat. No. 3,729,568. Other known uses of vitamin A acid which were reviewed by Thomas and Doyle in *Journal of American Academy of Dermatology* (May, 1981) Volume 4, No. 5, subsequent to completion of the present invention, include, in addition to acne treatment, treatment of senile comedones, nevus comedonicus, linear verrucous nevus, plantar warts, pseudofolliculitis, keratoacanthoma, solar keratosis of extremities, callosities, keratosis palmaris et plantaris, Darier's disease, ichthyosis, psoriasis, acanthosis nigricans, lichen planus, molluscum contagiosum, reactive perforating collagenosis, melasma, corneal epithelial peeling, geographic tongue, Fox-Fordyce disease, cutaneous metastatic melanoma and keloids or hypertrophic scars. Vitamin A acid derivatives (retinoids) are known to have prophylactic and therapeutic effects on a great variety of tumors and are being increasingly used as anti-tumor drugs.

In view of the foregoing, it is believed that vitamin A acid influences ultrastructural and proliferative properties of epidermal cells. However, these prior art uses of vitamin A acid have generally involved short term treatments in which relatively large doses of the acid are applied (i.e. sufficient to cause significant irritation and often peeling) in order to obtain a quick cure or treatment of the particular condition, such as removal of comedones, as opposed to persistent treatment of normal aging skin.

BRIEF SUMMARY OF THE INVENTION

The present invention relates to the use of low strength vitamin A acid (retinoic acid), known clinically as tretinoin, in moderating and preventing the aging changes of the exposed areas of the skin, especially the face. In particular, the methods of the present invention retard the effects of normal aging of the skin due to impairment of the differentiation of epidermal epithelial cells and due to loss of collagen fibers, abnormal changes in the elastic fibers and deterioration of small blood vessels of the dermis of the skin. The methods comprise applying topically to the epidermis of the skin effective amounts of vitamin A acid in a program of maintenance therapy, whereby epithelial growths are substantially reduced and prevented and the skin substantially regains and maintains its firmness, turgor and elasticity during the therapy. Generally, the maintenance therapy is begun in middle age when epithelial growths and other aging changes being to appear clinically.

The vitamin A acid may be applied to the skin in any suitable non-toxic, dermatologically acceptable vehicle, preferably a non-volatine, emollient or lubricating vehicle, in an amount and at a frequency which are insufficient to cause excessive irration of the skin. Generally, concentrations in the range of about 0.005 to 0.05% by weight of the vehicle are preferred.

DETAILED DESCRIPTION OF THE PREFERRED EMBODIMENTS

The purpose of this invention is to moderate and retard the aging changes in the skin by topical application of tretinoin beginning in middle age when aging changes first become evident clinically. Certain of the anatomic alterations can be corrected and at least partially reversed, accompanied by improvement in the appearance of the skin.

The invention accomplishes two goals. First, a prophylactic effect in preventing progression and worsening of the damage with the passage of time. Secondly, various abnormalities are corrected and modified to the extent that the structure and function of the skin acquires the characteristics of younger skin.

AGE ASSOCIATED STRUCTURAL CHANGES

Although many of the effects of the aging of the human skin are the result of underlying structural changes which build up over a period of years and can only be detected histologically prior to middle age, these changes and effects being to appear clinically about middle age, namely between about 35 and 45 years of age, and become more and more evident and pronounced thereafter. The more apparent effects of aging have already been referred to above, and each is associated with one or more underlying structural changes in the skin. For example, blotchiness or mottling (hyperpigmentation) is due to changes in the melanocytes in the population of epidermal cells. These pigment producing cells which, unlike the keratinocytes remain at the base of the epidermis lose their normal regulation process with aging and produce excess pigment which cause the blotchiness and mottling.

However, aside from such obvious cosmetic changes in the skin, there are a number of other changes which are more important though less apparent, including loss of sensory acuity and ability to heal wounds, decreased blood flow and decrease in the thickness of the skin. Older people have less sensitivity to pain and a longer response time. Thus, pain due to irritation or injury is not felt as soon or to the same extent as in young people with the result that superficialy minor but potentially serious injuries may be sustained without the individual being aware of the injury until serious damage has occured.

The surface temperature of the skin in older people is somewhat lower than the skin temperature in younger people, so that they often feel cold. This is due to a decrease in the blood supply to the skin due to loss of small blood vessels and decreased proliferation of new capillaries and small blood vessels in the skin. This is at least one of the causes of the loss of sensory acuity and response to pain. Furthermore, the decreased blood supply decreases the rate at which irritants and toxins are cleared from the skin tissue.

Still further, the skin of older people is more easily torn than that of younger people, since both the epidermis and dermis become thinner with age. As a result, there is less bulk to protect underlying organs and therefore more risk of serious injury. Moreover, when wounds or injuries are sustained, healing of the wounds is much slower in older people and may take as much as twice as long to heal as in younger persons.

The underlying causes of the above gross skin effects may be understood more readily from the following discussion of the specific changes in the epidermis and dermis as aging progresses.

1. Epidermis

With increasing age and exposure of a human to sun and other environmental traumas, cells divide at a slower rate (decreased capacity to renew themselves). They show marked irregularities in size, shape and staining properties; orderliness (polarity) from below to above is lost. The thickness of the epidermis decreases (atrophy). The horny layer which comprises the barrier against water loss and penetration of chemicals becomes abnormal due to the shedding (exfoliation) of cells in large group or clusters instead of as individual cells, resulting in roughness, scaling and dryness. There is loss of the orderly transformation of living epithelial cells into cornified dead cells which are shed at the surface, that is, differentiation is impaired. Aberrant differentiation results in numerous foci of abnormal epithelial growths or tumors, the most frequent and important of which are actinic keratoses. After many years these can transform into frank skin cancers called basal cell and squamous cell cancers. Pigment producing cells (melanocytes) can also become altered forming flat, dark growths (lentigo melanoma) which may progress to malignant melanoma. The cells which make up these premalignant growths are destroyed by topical tretinoin.

2. Dermis

The cells which make the fibers of the dermis become smaller and sparser with increasing age, usually in sundamaged facial skin. There is a great loss of collagen fibers resulting in looseness and easy stretchability of the skin; elastic fibers become abnormal so that the skin does not promptly snap back after being stretched. Since the fibrous components comprise more than 90% of the bulk of skin of which 95% is collagen, the degradation of these fibers, especially collagen, is mainly responsible for wrinkling, laxness and loss of elasticity.

Small blood vessels become thin walled, dilated and often ruptured. Vascular supply thereby becomes compromised.

BENEFICIAL EFFECTS OF TRETINOIN IN ACCORDANCE WITH THE PRESENT INVENTION (a) Increases proliferative activity of epidermal cells This results in thickening of the epidermis with correction of atrophy. Cell renewal is quickened so that cells divide at a rate typical of younger skin. Treatment with vitamin A acid in accordance with the invention can double the skin thickness. The stimulation of cell growth also results in faster wound healing. Experiments have been performed wherein blisters have been raised and cut off on skins of individuals of various ages. Healing takes place in 2 or 3 weeks in young people, but takes much longer in older persons. Application of tretinoin before raising the blister results in healing twice as fast in the older subjects.

(b) Corrects abnormalities of differentiation

Vitamin A acid regulates and controls the physiologic behavior of epithelial tissue, assuring its stability and integrity. It corrects and normalizes abnormalities of differentiation. In sundamaged skin, the numerous foci of abnormal growths and segments of atypical, abnormal epidermis are corrected, reversed or eliminated. Fewer growths appear and progression to cancer is halted. Normalizing of the epidermis results in a smoother, less dry and rough skin, since cells are not only produced more rapidly but exfoliation occurs by individual cells rather than clusters or scales, thus improving the topography of the skin. Moreover, hyperpigmentation resulting in blotches and splotches is reduced by tretinoin stopping excessive production of pigment by the melanocytes, although it cannot eliminate depigmentation.

(c) The metabolism of fibroblasts is increased

Fibroblasts synthesize the fibers of the dermis; new collagen is laid down, strengthening the physical foundation of the skin. Fibroblasts also make the ground substance which exists between the fibers, allowing these to glide past each other. The ground substance, known as acid mucopolysaccharides, is also responsible for the turgor and bounce of the skin. Tretinoin stimulates the formation of new acid mucopolysaccharides.

Accordingly vitamin A acid promotes the formation of a more normal dermis. Because of this activity, it has been found to promote and accelerate the healing of wounds in compromised tissue, of which regressed, aged dermis is an example. Further, the production of a new collagen layer not only repairs damaged skin but results in the effacement and prevention of fine wrinkles and lines.

(d) Vascularity is increased .

Tretinoin stimulates blood flow and promotes the formation of new vessels. Blood flow is greatly reduced in aged, sundamaged skin. A brisker blood supply improves the physiologic competence of the skin and imparts a livelier, glowing appearance. Patients often say their skin feels "more alive".

Several of the prior art treatments using vitamin A acid as referred to above have claimed there is an increase in the blood flow in the skin. However, the increased blood flow from such short term treatments could result simply from vasodilation caused by the irritating effects of high concentrations of vitamin A acid. In contrast, the low sub-irritating concentrations of vitamin A acid according to the present invention do not cause significant vasodilation, but it has been found that over the long term there is not only a proliferation of new blood vessels, but also an increase in lymphocytes and other blood cells. As a result, there are more cells to fight infection, and the increased blood supply allows the skin to clear irritants and toxins more quickly from the skin.

Still further, treatment with vitamin A acid according to the present invention raises the surface temperature of the skin by about ½ degree centigrade due to the greater basodermal flow of blood. The increased blood flow also increases acuity to pain and irritation, and the skin becomes more reactive to chemical insults. For example, experiments with highly drying and irritating cosmetics, soaps, perfumes, etc. have shown that young people will experience severe irritation within 3 or 4 days whereas it may take 2 or 3 weeks for an older person to feel the same irritation. The increased sensitivity of the skin treated with vitamin A acid provides an early warning system to older people so that too much damage is not done before the pain or irritation is felt.

Tretinoin may be formulated in bland, moisterizing bases, such as creams or ointments, usually in the concentration range of about 0.005% to 0.05% and preferably about 0.01% to 0.025% by weight of base, although higher concentrations may be used for darker skins. Other non-toxic, dermatologically acceptable vehicles or carriers in which tretinoin is stable will be evident to those of ordinary skill in the art. In general, emollient or lubricating vehicles, such as oleaginous substances, which help hydrate the skin are preferred. Volatile vehicles which dry or otherwise harm the skin, such as alcohol and acetone, should be avoided.

An ointment base (without water) is preferred in the winter and in subjects with very dry skin. Examples of suitable ointment bases are petrolatum, petrolatum plus volatile silicones, and lanolin.

In warm weather and often for younger persons, emulsion (cream) bases, which are mixtures of oils and water are preferred. Examples of suitable cream bases are Eucerin (Beiersdorf), cold cream (USP), Purpose Cream (J & J), and hydrophilic ointment (USP).

Tretinoin is a mild irritant and may cause redness and scaling, which may be accompanied by some tenderness and tightness. These reactions quickly disappear when the applications are stopped. However, even when applied excessively to produce an intense dermatitis, the reaction fades quickly leaving no permanent sequellae. Systemic side reactions are unknown. Selection of an appropriate emollient vehicle will more readily allow the use of a highly effective but sub-irritating dose of the vitamin A acid.

The extent or length of treatment according to the present invention may best be described as persistent or indefinite. That is, compared to the short term prior art treatments of various conditions with vitamin A acid in which the treatments are terminated as soon as the condition disappears or subsides, the treatment according to the present invention is intended to continue indefinitely, otherwise the effects of aging will reappear after treatment is terminated. That is, the treatments of the present invention may be considered to be intervention therapy in decelerating the aging process. If the intervention is stopped, there is regression to the original state.

Usually, there is little point in beginning the treatments of the present invention until middle age when the effects of aging begin to appear. The particular program of maintenance therapy according to the present invention will vary depending upon the individual being treated. Generally, depending upon the age and state of the skin when treatments begin, it has been found that once a day applications of vitamin A acid for up to 6 months may be necessary to reduce and control the effects of aging which have already occurred. Once a stabilized skin control has been obtained, the frequency of application of vitamin A acid may be reduced, for example to two or three times a week, and in some cases only once a week for the rest of the person's life. That is, once the aging process has been controlled, a maintenance dose on the order of two applications per week is generally sufficient to maintain that state.

The invention will be illustrated in more detail by reference to the following specific, non-limiting examples:

EXPERIMENTAL EXAMPLE 1

There has been applied 0.01% to 0.025% by weight concentrations of tretinoin in a base to the faces of middle-aged and elderly women. At least 500 persons have used typical tretinoin experimentally for periods ranging from three months to five years. These women were studied as follows:

About two hundred were inmates of the Philadelphia Home for the Indigent at Riverview. They ranged in age from 45 to 75. The creams or ointments were applied once daily before bedtime in an amount sufficient to achieve a continuous sustaining film. Clinical assessments were made once monthly. Beneficial effects were obtained in about 80% after about three months. Most of those who improved continued to use tretinoin daily for one to two years. Improvement was maximal at about six months and persisted as long as the drug was used. Withdrawal of the drug resulted in a slow loss of improvement with a return to the original state in about four to five months. Maintenance therapy was required to prevent relapse.

The beneficial effects included effacement of small wrinkles, smoother surface, greater turgor, elimination of actinic keratoes, elimination of senile comedones, less conspicuous pores and less mottling (fading of pigmented spots).

EXPERIMENTAL EXAMPLE 2

Histologic studies were conducted on twenty six residents of Riverview as follows. Tretinoin was applied to one side of the face once daily as in Experimental Example 1 for four to six months. The other side received the cream or ointment base alone.

Biopsies were taken from both sides at the end of the study and processed for histologic examination using a variety of histochemical stains. The tretinoin treated side was easily recognized in 24 of 26 subjects. The chief effects of tretinoin, as demonstrated by the indicated tissue staining techniques, were:

(a) Routine H & E stain: epidermis thicker, polarity restored, cells were regular size and shape, loss of atypia, no epidermal irregularities or pre-malignant growths, density of fibroblasts increased, more vessels.

(b) Fontanas stain for melanin: dispersion of pigment granules and far less pigment in epidermal cells.

(c) Reticulin stain: increase in young collagen fibers indicating deposition of new collegen.

(d) Orcein stain for elastin: moderate removal of degenerated elastic tissue, allowing intact fibers to be visualized more clearly.

(e) Hale's stain for ground substance: definite increase in acid mucopolysaccharides, especially in deeper dermis.

EXPERIMENTAL EXAMPLE 3

There have been treated at least another two hundred subjects in the aging skin clinic at the Hospital of the University of Pennsylvania. These are middle-class white women, ages 35 to 60. Tretinoin was applied as in Experimental Example 1 for at least six months.

Beneficial effects were clinically evident in about 80% of these persons. With this more sophisticated group we took note of subjective reactions as well. These women uniformly thought that their skin was livelier, smoother, fresher, and tighter. Again, we noted more turgor, effacement of fine lines, less hyperpigmentation, more youthful appearance, less roughness, less wrinkling.

EXPERIMENTAL EXAMPLE 4

About one hundred pain volunteers recruited at Ivy Research Laboratories have been studied in a variety of ways including biopsies, physiologic tests, etc. The importance of this series is that the tests were conducted according to the double-blind format and hence were strictly controlled. Tretinoin was applied once daily as in Experimental Example 1 for six to twelve months to one side of the face; the other side received the unmedicated vehicle. The applications were made five days a week by a trained monitor who did not know which of the two preparations contained the active agent. The clinical observations were made without knowledge of the drug treated side.

When the code was broken, some improvement was noted in about 15% of cases treated with the vehicle alone. Distinctly beneficial effects were secured in about 85% on the tretinoin treated side. Histologic study in thirteen cases confirmed the clinical results of restoration to a more normal pattern on the tretinoin side. The epidermal and dermal changes were those described above.

Fluorescein injected into both sides was removed in about half the time on the tretinoin side. This indicates improved vascularity resulting in faster clearance of drugs from the skin. Moreover, a series of clinical stimuli indicate that tretinoin treated skin is more reactive, showing behaviors more typical of young skin. It responds more rapidly and intensely to irritant chemicals such as croton oil and dimethylsulfoxide; it blushes more readily after application of nicotinate; blisters raised by ammonium hydroxide heal more quickly (greater wound healing, a known effect of tretinoin); and contact allergic rections (poison ivy) also heal more quickly.

EXPERIMENTAL EXAMPLE 5

The rhino mouse is a hairless species with abnormally wrinkled skin. Topical application of tretinoin in 0.01% to 0.025% concentration virtually eliminates wrinkling in three to four weeks. The skin becomes fuller and more turgid.

The improvement is largely a result of increased ground substance and greater water content. The epidermis thickens and certain epithelial abnormalities regress. These beneficial effects are surprisingly similar to those in human skin suggesting that this is an appropriate model, especially in regard to wrinkling and looseness of skin.

From the foregoing, it will be seen that the invention has the following advantages inter alia:
  A. Clinical
    Effacement of fine wrinkles
    Smoother surface
    Lightens pigmented blotches
    Skin has more turgor
    Large pores less noticeable
    Skin feels livelier
  B. Histologic
    Thicker epidermis
    Normalizes atypia and pre-malignant changes.
    Atrophy and dysplasia corrected.
    Stimulates blood flow; new vessels formed
    Stimulates fibroblasts with new collagen formation
    Increases ground substance
    Melanin within keratinocytes is decreased It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

I claim:

1. A method for retarding and reversing the loss of collagen fibers, abnormal changes in elastic fibers, the deterioration of small blood vessels, and the formation of abnormal epithelial growths in sundamaged human skin, comprising applying topically to the epidermis of the skin a composition comprising effective amounts of vitamin A acid in an emollient vehicle in a program of maintenance therapy, whereby the skin substantially regains and maintains its firmness, turgor and elasticity during said therapy, said composition and amounts of vitamin A acid being selected so as to provide a sub-irritating dose of vitamin A acid.

2. A method according to claim 1 wherein said skin is human facial skin.

* * * * *